US011825907B2

(12) United States Patent
Roh et al.

(10) Patent No.: US 11,825,907 B2
(45) Date of Patent: Nov. 28, 2023

(54) METHOD AND APPARATUS FOR DETERMINING SENSORY THRESHOLD FOR SHOE-TYPE DEVICE, SHOE-TYPE DEVICE, AND METHOD OF CONTROLLING THE SAME

(71) Applicants: Samsung Electronics Co., Ltd., Suwon-si (KR); SEOUL NATIONAL UNIVERSITY R&DB FOUNDATION, Seoul (KR)

(72) Inventors: Segon Roh, Suwon-si (KR); Jeongin Moon, Seoul (KR); Prabhat Pathak, Seoul (KR); Jooeun Ahn, Seoul (KR); Changhyun Roh, Suwon-si (KR); Youngbo Shim, Suwon-si (KR)

(73) Assignees: Samsung Electronics Co., Ltd., Gyeonggi-do (KR); Seoul National University R&DB Foundation, Seoul (KR)

( * ) Notice: Subject to any disclaimer, the term of this patent is extended or adjusted under 35 U.S.C. 154(b) by 535 days.

(21) Appl. No.: 16/992,382

(22) Filed: Aug. 13, 2020

(65) Prior Publication Data

US 2021/0186141 A1 Jun. 24, 2021

(30) Foreign Application Priority Data

Dec. 19, 2019 (KR) ........................ 10-2019-0170835

(51) Int. Cl.

*A43B 3/34* (2022.01)
*A61B 5/00* (2006.01)
*A61B 5/103* (2006.01)

(52) U.S. Cl.

CPC .............. *A43B 3/34* (2022.01); *A61B 5/0051* (2013.01); *A61B 5/1038* (2013.01); *A61B 5/6807* (2013.01); *A61B 2562/0247* (2013.01)

(58) Field of Classification Search

CPC ...... A61B 5/6807; A61B 5/0048–0057; A61B 5/4023; A61B 5/4824; A61B 5/4827;

(Continued)

(56) References Cited

U.S. PATENT DOCUMENTS

2004/0173220 A1 9/2004 Harry et al.
2006/0178596 A1* 8/2006 Robichaud ........... A61B 5/0053 600/587

(Continued)

FOREIGN PATENT DOCUMENTS

CN 102316802 A 1/2012
KR 10-1004001 B1 12/2010

(Continued)

OTHER PUBLICATIONS

International Search Report dated Oct. 15, 2020 for the corresponding International Application No. PCT/KR2020/009162.

(Continued)

*Primary Examiner* — Kaylee R Wilson
*Assistant Examiner* — Raymond P Dulman
(74) *Attorney, Agent, or Firm* — HARNESS, DICKEY & PIERCE, P.L.C.

(57) ABSTRACT

A method and apparatus for determining sensory threshold information for a shoe-type device, the shoe-type device, and a method of controlling the shoe-type device are disclosed. The method of determining sensory threshold information includes executing a program for sensory threshold testing, determining sensory threshold information of a user based on a choice input by the user that is received in a process of the sensory threshold testing, and transmitting the determined sensory threshold information to the shoe-type device.

25 Claims, 11 Drawing Sheets

Start

510 Execute program for sensory threshold testing

520 Determine sensory threshold information of user based on choice input by user 530 Transmit determined sensory threshold information to shoe-type device End

(58) Field of Classification Search
CPC ...... A61B 5/483; A61B 5/4833; A61H 23/00; A61H 2302/002
USPC .................................................. 600/552–557
See application file for complete search history.

(56) References Cited

U.S. PATENT DOCUMENTS

| | | | | |
|---|---|---|---|---|
| 2008/0193905 | A1* | 8/2008 | Leung .................... | G09B 23/30 901/46 |
| 2011/0271554 | A1 | 11/2011 | Jazdanian | |
| 2011/0313314 | A1* | 12/2011 | Gefen .................... | A61B 5/441 600/555 |
| 2012/0186101 | A1 | 7/2012 | Sanchez | |
| 2015/0068069 | A1* | 3/2015 | Tran ......................... | A43B 3/34 340/693.1 |
| 2017/0112712 | A1 | 4/2017 | Chawan et al. | |
| 2017/0266443 | A1* | 9/2017 | Rajguru ................... | A61B 5/24 |
| 2018/0085055 | A1* | 3/2018 | Annoni ................ | A61B 5/7475 |

FOREIGN PATENT DOCUMENTS

| | | | | | |
|---|---|---|---|---|---|
| KR | 10-2015-0102177 | A | | 9/2015 | |
| KR | 10-2016-0085109 | A | | 7/2016 | |
| KR | 10-2018-0117376 | A | | 10/2018 | |
| RU | 2589543 | C1 | * | 7/2016 | ........... A61B 5/0051 |
| WO | WO-2017216812 | A1 | * | 12/2017 | ........... A61B 5/0051 |

OTHER PUBLICATIONS

Written Opinion dated Oct. 15, 2020 for the corresponding International Application No. PCT/KR2020/009162.

R. Mildren et al., "Foot sole skin vibration perceptual thresholds are elevated in a standing posture compared to sitting" Gait & Posture, 43, (2016) pp. 87-92.

Teasdale, N. et al., "Attentional demands for postural control: the effects of agin and sensory reintegration", Gait and Posture, vol. 14, p. 203-210, (2001).

* cited by examiner

METHOD AND APPARATUS FOR DETERMINING SENSORY THRESHOLD FOR SHOE-TYPE DEVICE, SHOE-TYPE DEVICE, AND METHOD OF CONTROLLING THE SAME

CROSS-REFERENCE TO RELATED APPLICATION

This application claims under 35 U.S.C. § 119 to Korean Patent Application No. 10-2019-0170835 filed on Dec. 19, 2019, in the Korean Intellectual Property Office, the entire contents of which are incorporated herein by reference in their entirety.

BACKGROUND

1. Field

At least one example embodiment relates to a method of setting sensory threshold information for a shoe-type device, a terminal device configured to perform same, a method of operating the shoe-type device, and/or the shoe-type device.

2. Description of the Related Art

A user wears shoes in daily life. The shoes have a basic function of protecting the feet of the user comfortably and safely. Recently, shoes having a special function in addition to such a basic function have been developed and released. For example, there are various types of shoes, for example, shoes that automatically provide an electric stimulus to soles of the feet of a user when the user walks with the shoes on, and shoes that detect a gait pattern of a user through a sensor. As such, shoes have evolved into wearable devices having various advanced functions.

SUMMARY

Some example embodiments relate to method of setting sensory threshold information for a shoe-type device worn by a user.

In some example embodiments, the method includes instructing the shoe-type device to provide a stimulus to the user during a sensory threshold test; determining the sensory threshold information of the user based on an input from the user received in response to providing the stimulus to the user during the sensory threshold test; and transmitting the sensory threshold information to the shoe-type device.

In some example embodiments, the determining of the sensory threshold information includes determining a sensory threshold value for each of a left foot and a right foot of the user.

In some example embodiments, the determining of the sensory threshold information includes determining the sensory threshold value for each of a forefoot and a rearfoot of the left foot of the user, and a forefoot and a rear foot of the right foot of the user.

In some example embodiments, the determining of the sensory threshold information includes performing a first test by instructing the shoe-type device to provide the stimulus to the user to determine a reference sensory threshold value for a foot of the user based on the input from the user; and performing a second test by instructing the shoe-type device to provide the stimulus to the user to determine a final sensory threshold value for the foot of the user based on the reference sensory threshold value.

In some example embodiments, the performing the second test includes instructing the shoe-type device to provide the stimulus to the user such that a change in an intensity of the stimulus applied to the foot of the user during the second test over time is less than a change in the intensity of the stimulus applied to the foot of the user during the first test over time.

In some example embodiments, the performing of the first test includes transmitting, to the shoe-type device, a control signal instructing the shoe-type device to apply a test vibration to a current sole portion among a plurality of sole portions of the foot of the user; receiving an input from the user indicating a selected one of the plurality of sole portions; and determining whether the current sole portion corresponds to the selected one of the plurality of sole portions.

In some example embodiments, the method further includes randomly selecting a next sole portion to receive the test vibration from among the plurality of sole portions, in response to the current sole portion corresponding to the selected one of the plurality of sole portions.

In some example embodiments, the method further includes transmitting, to the shoe-type device, a control signal instructing the shoe-type device to again apply the test vibration to the current sole portion, in response to the current sole portion not corresponding to the selected one of the plurality of sole portions.

In some example embodiments, an initial intensity of the test vibration applied to the current sole portion is based on an intensity of the test vibration most recently applied to the current sole portion.

In some example embodiments, the performing the second test includes repeatedly performing the second test to obtain a plurality of sensory threshold values; and determining the final sensory threshold value based on the plurality of sensory threshold values.

In some example embodiments, the performing of the first test includes determining an intensity of a test vibration in a range between a minimum intensity and a maximum intensity; and transmitting, to the shoe-type device, a control signal instructing the shoe-type device to apply the test vibration of the determined intensity to the foot of the user through a vibrator of the shoe-type device.

In some example embodiments, the determining of the intensity of the test vibration includes increasing the intensity of the test vibration, in response to not receiving the input from the user.

In some example embodiments, the performing of the second test includes transmitting, to the shoe-type device, a control signal instructing the shoe-type device to apply a test vibration to a current sole portion among a plurality of sole portions of the foot of the user based on the reference sensory threshold value; receiving an input from the user indicating a selected one of the plurality of sole portions; and determining whether the current sole portion corresponds to the selected one of the plurality of sole portions.

In some example embodiments, the method further includes randomly selecting a next sole portion to receive the test vibration from among the plurality of sole portions, in response to the current sole portion corresponding to the selected one of the plurality of sole portions.

In some example embodiments, the method further includes transmitting, to the shoe-type device, a control signal instructing the shoe-type device to again apply the test vibration to the current sole portion, in response to the current sole portion not corresponding to the selected one of the plurality of sole portions.

In some example embodiments, an initial intensity of the test vibration applied to the current sole portion is based on an intensity of the test vibration most recently applied to the current sole portion.

In some example embodiments, the performing of the second test includes determining an intensity of a test vibration based on the reference sensory threshold value; and transmitting, to the shoe-type device, a control signal instructing the shoe-type device to apply the test vibration of the determined intensity to the foot of the user through a vibrator of the shoe-type device.

In some example embodiments, the determining of the intensity of the test vibration includes increasing the intensity of the test vibration, in response to not receiving the input from the user.

In some example embodiments, the transmitting of the sensory threshold information includes transmitting the sensory threshold information to the shoe-type device via Bluetooth communication.

Some example embodiments relate to a method of operating a shoe-type device to provide a stimulus to a user.

In some example embodiments, the method includes receiving, from a terminal device, sensory threshold information of the user, the sensory threshold information determined via a sensory threshold test; and controlling a plurality of vibrators included in the shoe-type device based on the sensory threshold information to provide the stimulus to the user.

In some example embodiments, the sensory threshold information includes a sensory threshold value determined through the sensory threshold test for each of a left forefoot of the user, a left rearfoot of the user, a right forefoot of the user, and a right rearfoot of the user.

In some example embodiments, the sensory threshold test includes, a first test to determine a reference sensory threshold value for a foot of the user based on a input received from the user, and a second test to determine a final sensory threshold value for the foot of the user based on the reference sensory threshold value.

Some example embodiments relate to a non-transitory computer-readable medium storing computer readable instructions that, when executed by a computer, causes the computer to perform the method of setting sensory threshold information for a shoe-type device worn by a user.

Some example embodiments relate to a terminal device.

In some example embodiments, the terminal device includes a communication device configured to communicate with a shoe-type device worn by a user; and a processor configured to, instruct the shoe-type device to provide a stimulus to the user during sensory threshold test, determine sensory threshold information of the user based on an input from the user received in response to providing the stimulus to the user during the sensory threshold test, and transmit, via the communication device, the sensory threshold information to the shoe-type device.

In some example embodiments, the processor is configured to determine the sensory threshold information by determining, through the sensory threshold test, a sensory threshold value of each of a left forefoot of the user, a left rearfoot of the user, a right forefoot of the user, and a right rearfoot of the user.

In some example embodiments, the processor is configured to determine the sensory threshold information by, performing a first test by instructing the shoe-type device to provide the stimulus to the user to determine a reference sensory threshold value for a foot of the user based on the input from the user, and performing a second test by instructing the shoe-type device to provide the stimulus to the user to determine a final sensory threshold value for the foot of the user based on the reference sensory threshold value.

Some example embodiments relate to a shoe-type device.

In some example embodiments, the shoe-type device includes at least one vibrator configured to generate a vibration; a communication device configured to receive, from a terminal device, sensory threshold information of a user, the sensory threshold information determined via a sensory threshold test; and a controller configured to control the at least one vibrator to generate the vibration based on the sensory threshold information.

In some example embodiments, the sensory threshold test includes, a first test to determine a reference sensory threshold value for a foot of the user based on an input from the user, and a second test to determine a final sensory threshold value for the foot of the user based on the reference sensory threshold value.

In some example embodiments, the at least one vibrator is configured to generate the vibration such that an intensity of the vibration less than a sensory threshold of the user wearing the shoe-type device determined based on the sensory threshold information.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
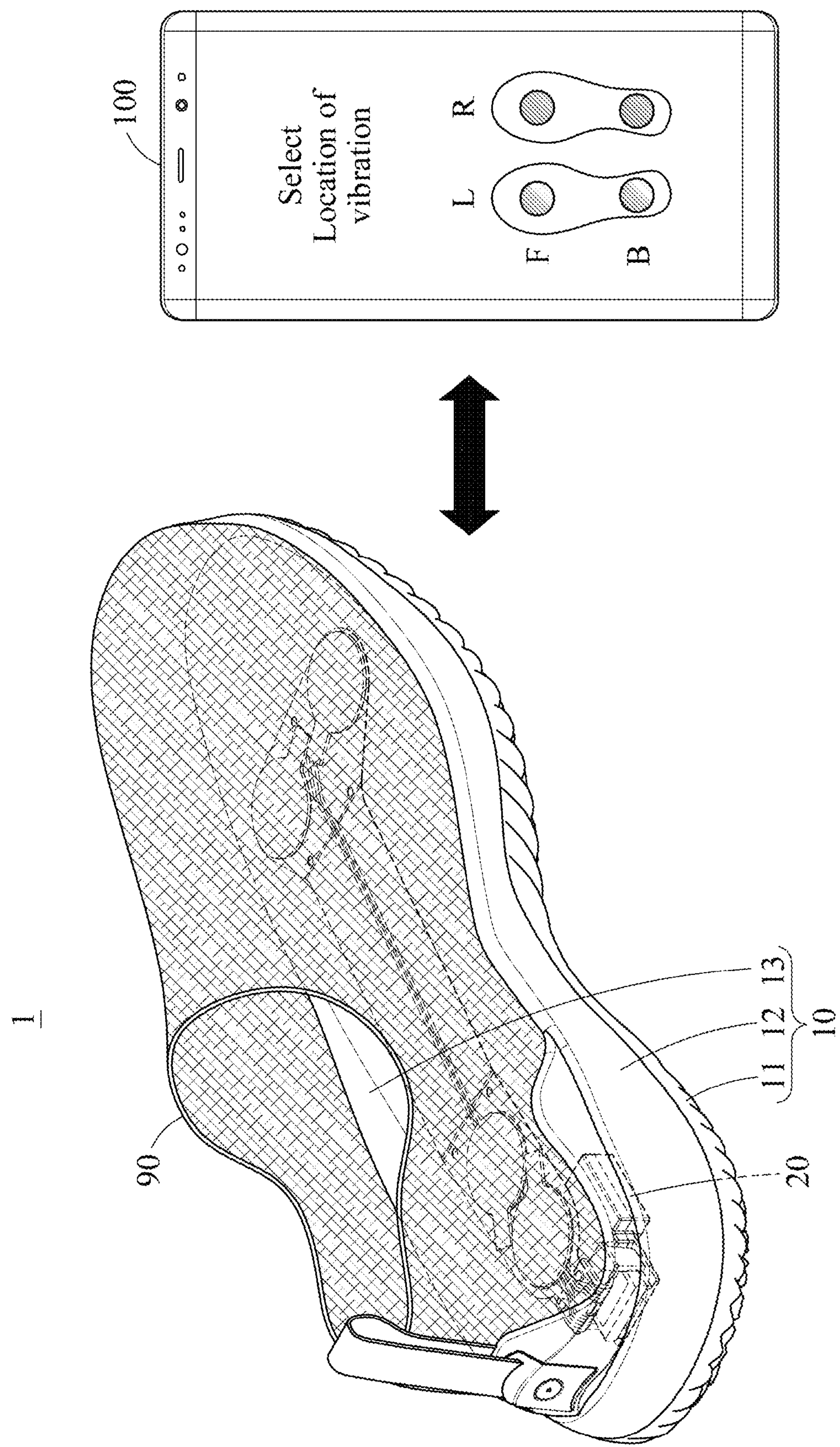
FIG. 1 is a diagram illustrating an example of how a shoe-type device and a terminal device operate according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected," "coupled," or "joined" to another component, a third component may be "connected," "coupled," and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms, including technical and scientific terms, used herein have the same meaning as commonly understood by one of ordinary skill in the art to which the disclosure of this application pertains. Terms, such as those defined in commonly used dictionaries, are to be interpreted as having a meaning that is consistent with their meaning in the context of the relevant art, and are not to be interpreted in an idealized or overly formal sense unless expressly so defined herein.

Also, in the description of example embodiments, detailed description of structures or functions that are thereby known after an understanding of the disclosure of the present application will be omitted when it is deemed that such description will cause ambiguous interpretation of the example embodiments.

Various example embodiments will now be described more fully with reference to the accompanying drawings in which some example embodiments are shown. In the drawings, the thicknesses of layers and regions are exaggerated for clarity.

A shoe-type device to be described hereinafter may include an electronic device configured to generate a vibration. For example, the shoe-type device may include a vibrator that may generate vibration noise by generating a physical vibration based on a control signal. The vibrator may be embedded in the shoe-type device, or an insole, and provide a user wearing the shoe-type device with a stimulus of a magnitude less than a sensory threshold of the user. The sensory threshold refers to a minimum magnitude of a stimulus that activates cells. The vibrator may generate the vibration noise having an intensity less than or equal to a threshold of a tactile sensation felt by a plantar sole of a foot of the user, thereby triggering stochastic resonance. The stochastic resonance refers to a phenomenon where a level of sensitivity to a target signal for observation is improved when, to a measuring device or a sensory organ having a fixed sensory threshold, white noise of a magnitude less than or equal to the sensory threshold is applied. For example, the vibration noise generated by the vibrator of the shoe-type device may amplify a tactile signal to be transferred to the plantar sole of the user through the stochastic resonance, and thus the user may feel more sensitively a sensation on the plantar sole of the user. Thus, the shoe-type device may help those who may not normally feel a sensation due to a reduced sensory ability of their feet. In addition, the shoe-type device may help increase the postural balance of a user and increase walking stability through the stochastic resonance triggered by the shoe-type device.

Hereinafter, example embodiments will be described in detail with reference to the accompanying drawings, and like reference numerals in the drawings refer to like elements throughout.

Figure 2:
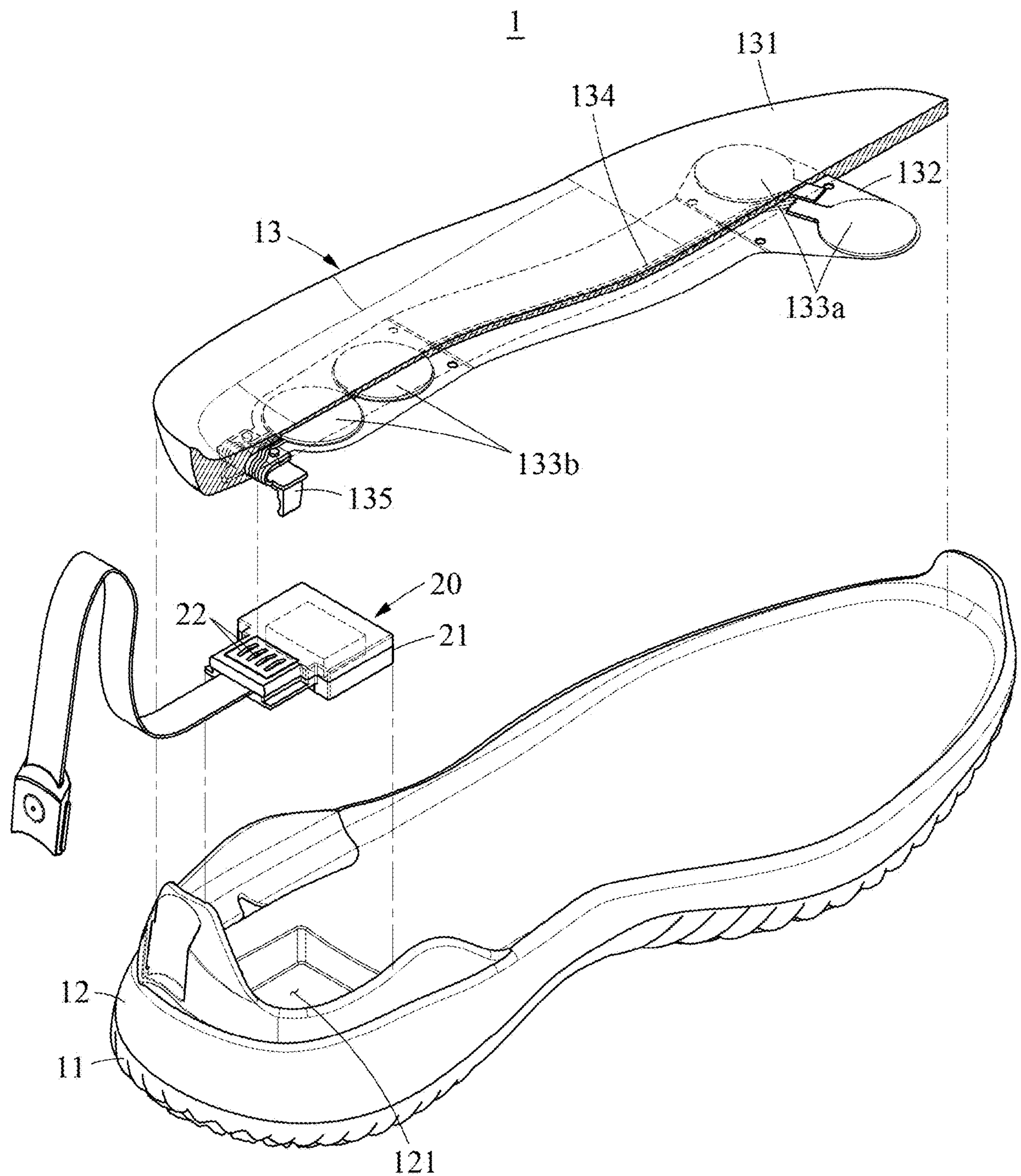
FIG. 2 is an exploded perspective view of an example of a shoe-type device according to at least one example embodiment.
Figure 3:
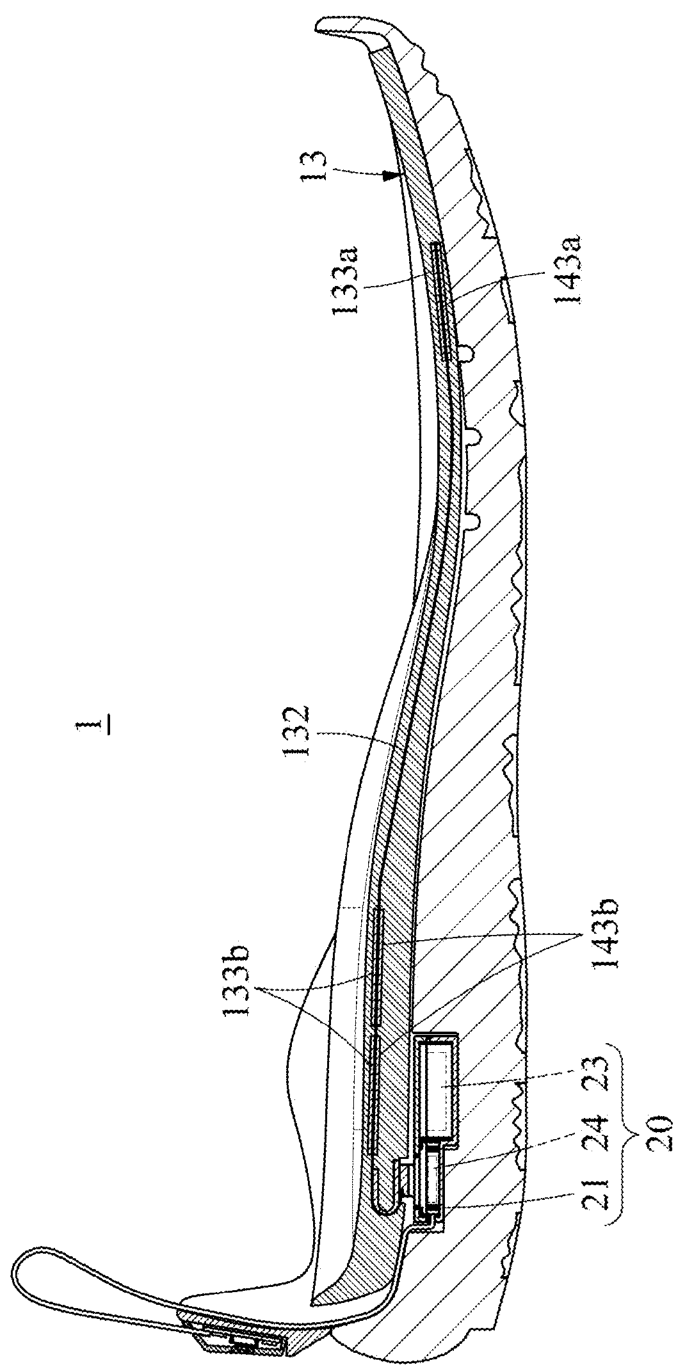
FIG. 3 is a cross-sectional view of an example of a shoe-type device according to at least one example embodiment.

FIG. 1 is a diagram illustrating an example of how a shoe-type device and a terminal device operate according to at least one example embodiment. FIG. 2 is an exploded perspective view of an example of a shoe-type device with an insole body being separately shown according to at least one example embodiment. FIG. 3 is a cross-sectional view of an example of a shoe-type device according to at least one example embodiment.

Referring to FIGS. 1 through 3, a shoe-type device 1 includes a sole 10, a control device 20, and an upper 90. The sole 10 includes an outsole 11, a midsole 12, and an insole 13. The shoe-type device 1 is provided in a form of a shoe, for example. However, the form of the shoe-type device 1 is not limited to the foregoing example. For example, the shoe-type device 1 may be provided in a form of a sock, and be applied to an exercise assist robot.

The outsole 11 forms at least a portion of a bottom part of the shoe-type device 1. For example, the outsole 11 includes a bottom surface that is brought into contact with the ground when a user wears the shoe-type device 1. Although the outsole 11 and the midsole 12 will be described hereinafter as being separate, the outsole 11 and the midsole 12 may be provided in an integral form. The midsole 12 forms at least a portion of an outer lower shape of the shoe-type device 1. The insole 13 is provided inside the upper 90, and disposed on the midsole 12. The insole 13 includes a surface that is brought into contact with a plantar sole of a foot of the user when the user wears the shoe-type device 1, and is detachable from the midsole 12.

The insole 13 includes an insole body 131, a support layer 132, an electronic device, a connecting line 134, and a connector 135. The insole body 131 is disposed on a top surface of the midsole 12, and may be manufactured in various shapes. The support layer 132 is provided on an inner side of the insole body 131 and may support the electronic device and the connecting line 134. The connecting line 134 may electrically connect the electronic device and the control device 20. The connector 135 may electrically connect each electronic device to the control device 20.

The electronic device is disposed on a top surface of the support layer 132. The electronic device and the support layer 132 are disposed as a whole in the insole body 131. However, examples are not limited to the illustrated example, and a portion of the electronic device may be exposed to an outside of the insole body 131.

The electronic device includes at least one vibrator, for example, a vibrator 133*a* and a vibrator 133*b* as illustrated, and at least one pressure sensor, for example, a pressure sensor 143*a* and a pressure sensor 143*b* as illustrated. The vibrators 133*a*, 133*b* may include, for example, a piezoelectric motor (or simply piezo motor) or an eccentric vibration motor. The vibrators 133*a* and 133*b* may generate a physical vibration having an intensity less than or equal to a set maximum vibration intensity. The intensity may change irregularly as in noise, for example. The pressure sensor 143*a* and 143*b*, which is a sensor configured to measure a pressure, may sense a foot pressure to be transferred from the plantar sole of the user when the user wears the shoe-type device 1. The pressure sensor 143*a* and 143*b* may be a piezoelectric pressure sensor (or simply piezo pressure sensor) or a force sensitive resistor (FSR) pressure sensor, and be embodied in a form of a film. According to an example embodiment, the pressure sensor 143*a* and 143*b* may be disposed under where the vibrator is disposed. For example, as illustrated, the pressure sensors 143*a* and 143*b* are disposed respectively under where the vibrators 133*a* and 133*b* are disposed.

According to an example, the electronic device may further include another sensor, for example, an inertial sensor such as an acceleration sensor and a gyro sensor. The inertial sensor may be used to measure a movement of the shoe-type device 1 or a movement of the user wearing the shoe-type device 1. The electronic device may be electrically connected to the control device 20, and thus sensor data may be transferred from the pressure sensor and the other sensor to the control device 20.

The control device 20 includes a case 21, a connecting portion 22, a battery 23, and a controller 24. The case 21 is provided in a form corresponding to a receiving groove 121 formed in the midsole 12. The connecting portion 22 includes a terminal to be electrically connected to the connecting line 134, and is disposed on an upper side of the case 21.

The battery 23 may provide power that is needed for the shoe-type device 1 to operate. For example, the battery 23 may provide power to the electronic device and the controller 24, and include a rechargeable battery. The controller 24 includes at least one processor, and may control an operation of the shoe-type device 1. The controller 24 may generate a control signal to control an operation of the electronic device. For example, the controller 24 may generate a control signal for controlling the vibrator based on a pressure measured by the pressure sensors 143*a* and 143*b*, and a control signal for adjusting the number of vibrations to be generated by the vibrators 133*a* and 133*b* and/or a maximum vibration intensity.

In addition, the control device 20 includes a communication device (not shown). The communication device may communicate with a terminal device 100 through wireless communication, for example, Bluetooth communication, or through wired communication using a cable. For example, the communication device may include a wireless transmission antenna and a wireless reception antenna for wireless communication, and may wirelessly transmit and receive data and information to and from the terminal device 100 through these antennas.

The terminal device 100 may communicate with the communication device having a communication function described above. The terminal device 100 may remotely control the shoe-type device 1. For example, the terminal device 100 may perform a control function, for example, a power on/off control function, a timer setting function, and a vibration intensity adjusting function, for the shoe-type device 1 based on an input to be received from the user. In addition, the terminal device 100 may execute a program or an application for performing a test to determine or measure sensory threshold information of the user, and transmit the sensory threshold information determined through the test to the shoe-type device 1 through wireless communication. The terminal device 100 may be, for example, a cellular phone, a smartphone, a personal computer (PC), a laptop, a netbook, a tablet PC, a personal digital assistant (PDA), a wearable device, or other electronic devices that may communicate with the shoe-type device 1.

A function of vibrating the plantar sole of the user by the vibrator of the shoe-type device 1 may trigger stochastic resonance as described above, thereby improving a sensory function of the user wearing the shoe-type device 1. However, a sensory threshold may differ from individual to individual. In addition, even for the same user, a sensory threshold of a left foot of the user may differ from a sensory threshold of a right foot of the user. In addition, even for the same foot, a sensory threshold of a forefoot may differ from a sensory threshold of a rearfoot.

Thus, to effectively provide an effect of such stochastic resonance to a user, in one or more example embodiments, a sensory threshold of a user who will wear the shoe-type device 1 may be measured and, for example, utilized to control the shoe-type device 1.

According to example embodiments to be described hereinafter, a user may accurately and reliably measure a sensory threshold of a plantar sole of the user without any help from others through a sensory threshold test executed using the terminal device 100. In addition, the user may accurately and reliably measure a sensory threshold of each of a left foot and a right foot of the user, and also a sensory threshold of each of various portions of each foot, through the sensory threshold test.

Figure 4:
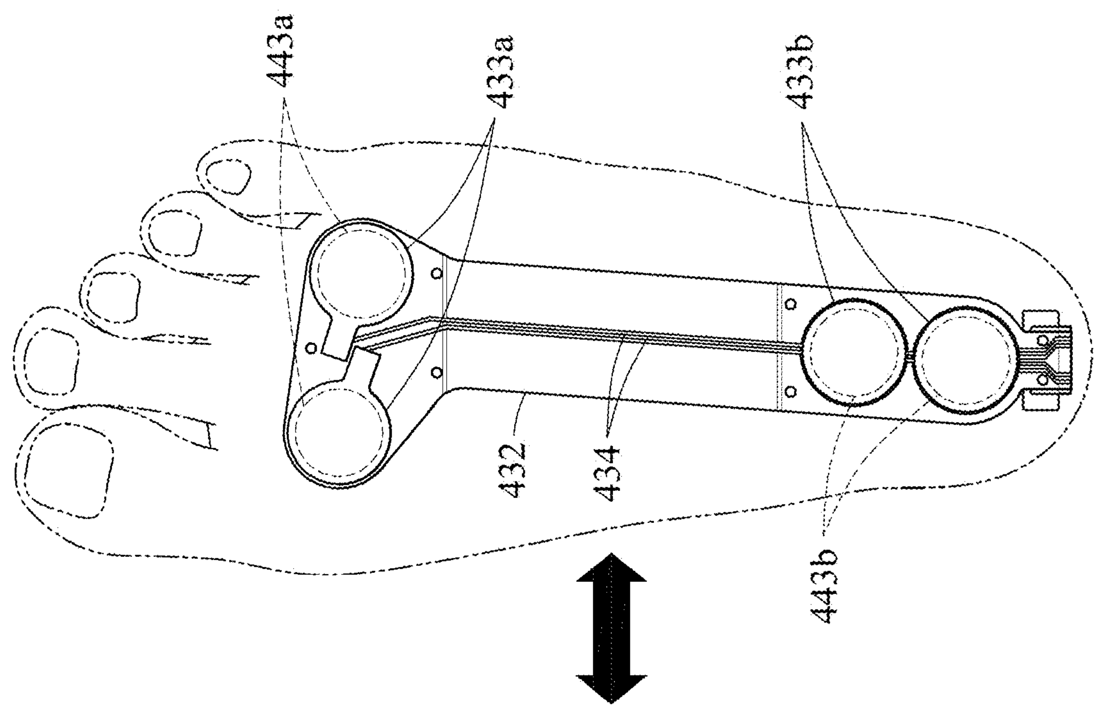
FIG. 4 is a diagram illustrating an example of sensory threshold testing through interworking between a shoe-type device and a terminal device according to at least one example embodiment.
Figure 4:
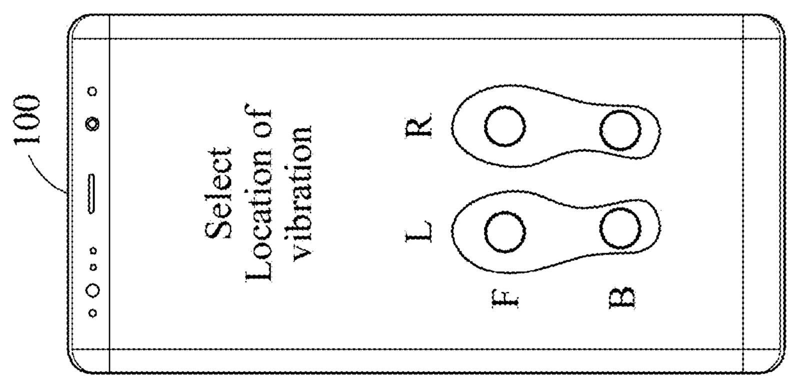
Figure 4:
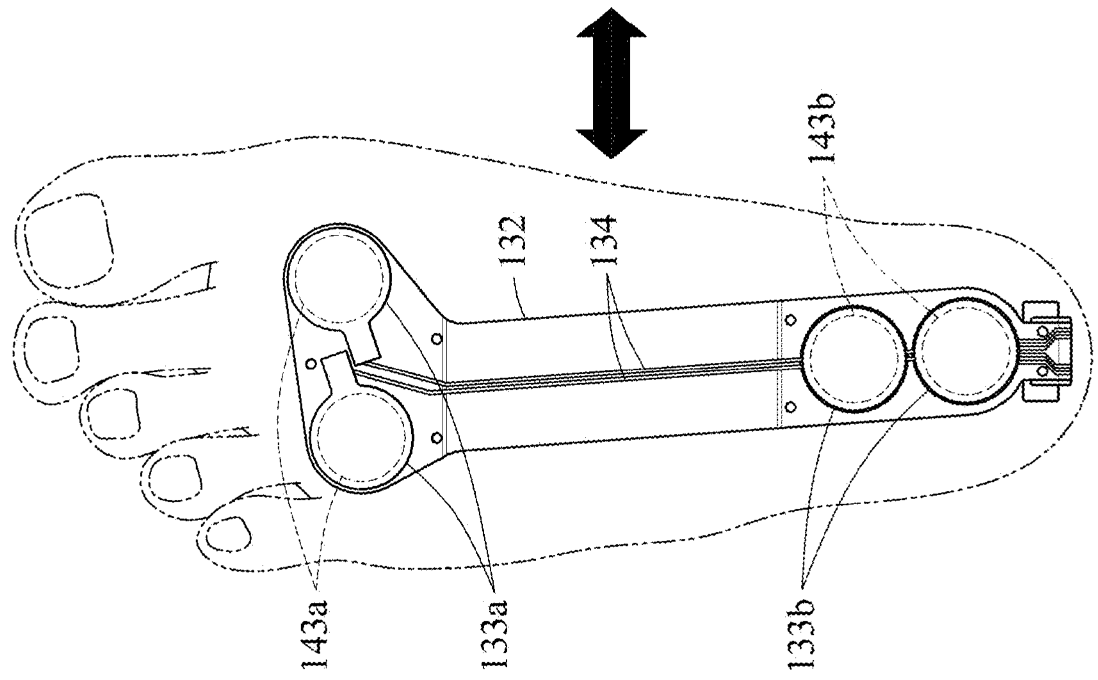

FIG. 4 is a diagram illustrating an example of sensory threshold testing through interworking between a shoe-type device and a terminal device according to at least one example embodiment.

Referring to FIG. 4, a shoe-type device worn on a left foot of a user includes the front vibrator 133*a* disposed in a front portion of the support layer 132, the rear vibrator 133*b* disposed in a rear portion of the support layer 132, the front pressure sensor 143*a* disposed under the front vibrator 133*a*, and the rear pressure sensor 143*b* disposed under the rear vibrator 133*b*. The front vibrator 133*a* may generate a vibration at a location corresponding to a left forefoot of the user, and the rear vibrator 133*b* may generate a vibration at a location corresponding to a left rearfoot of the user. Here, the left forefoot of the user may indicate an anterior sole portion of the left foot of the user, and the left rearfoot of the user may indicate a posterior sole portion of the left foot of the user.

Similarly, the shoe-type device worn on a right foot of the user includes a front vibrator 443*a* disposed in a front portion of a support layer 432, a rear vibrator 433*b* disposed in a rear portion of the support layer 432, a front pressure sensor 443*a* disposed under the front vibrator 433*a*, and a rear pressure sensor 443*b* disposed under the rear vibrator 433*b*. The front vibrator 433*a* may generate a vibration at a location corresponding to a right forefoot of the user, and the rear vibrator 433*b* may generate a vibration at a location corresponding to a right rearfoot of the user. Here, the right forefoot of the user may indicate an anterior sole portion of the right foot of the user, and the right rearfoot of the user may indicate a posterior sole portion of the right foot of the user.

According to an example embodiment, the user may measure a sensory threshold value for each of the left foot and the right foot through sensory threshold testing using the terminal device 100. In a process of the sensory threshold testing, a test vibration may be generated through one of the front vibrator 133*a* corresponding to the left forefoot, the rear vibrator 133*b* corresponding to the left rearfoot, the front vibrator 433*a* corresponding to the right forefoot, and the rear vibrator 433*b* corresponding to the right rearfoot. The user may then select a sole portion in/from which the user senses the test vibration through a sensory threshold testing program that is executed in the terminal device 100. In the process of the sensory threshold testing, an intensity of a vibration of a vibrator may gradually increase until the user senses the vibration, and a sensory threshold value of a corresponding sole portion of the user may be determined based on an intensity at which the user senses the vibration. In the sensory threshold testing program, a test may be performed based on a random choice from among the vibrators 133*a*, 133*b*, 433*a*, and 433*b*, similarly to a blind test. Here, information associated with the selected vibrator may not be provided to the user. Through this, it is possible to accurately estimate a sensory threshold of each of the left foot and the right foot of the user, and quantify a sensory threshold of each of the forefoot of the left foot, the rearfoot of the left foot, the forefoot of the right foot, and the rearfoot of the right foot. The sensory threshold testing will be described hereinafter with reference to FIGS. 6 through 9.

Figure 5:
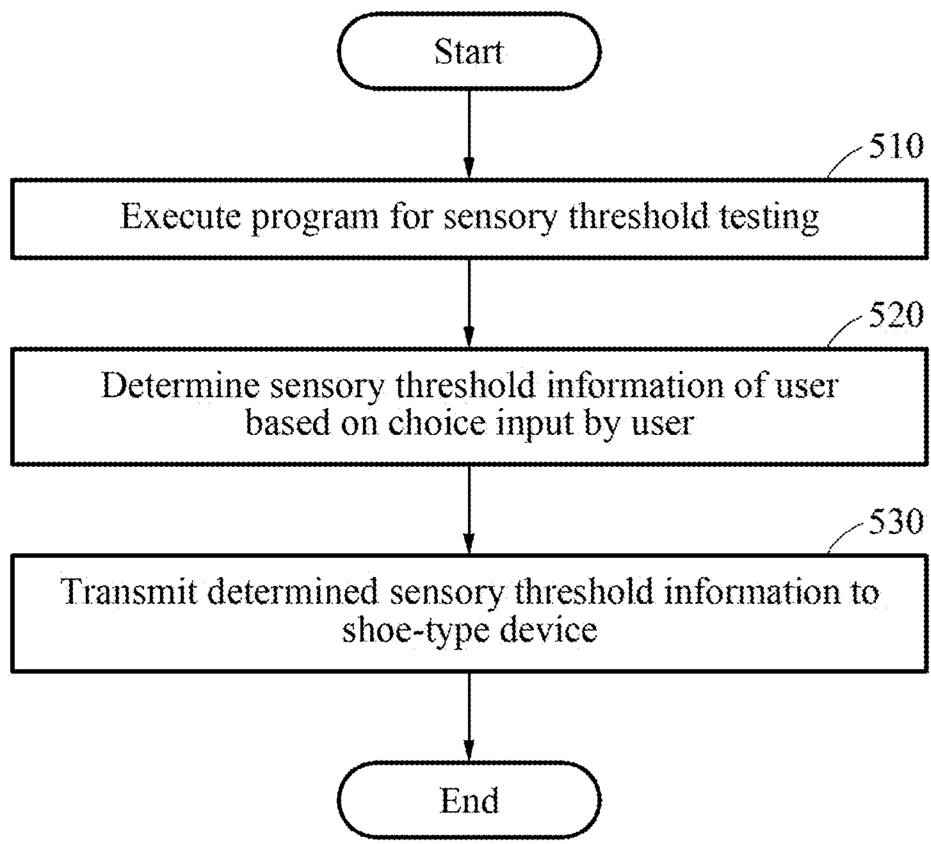
FIG. 5 is a flowchart illustrating an example of a method of determining sensory threshold information according to at least one example embodiment.

FIG. 5 is a flowchart illustrating an example of a method of determining sensory threshold information according to at least one example embodiment. The method of determining sensory threshold information to be described hereinafter with reference to FIG. 5 may be performed by a terminal device described herein.

Referring to FIG. 5, in operation 510, the terminal device 100 executes a program for sensory threshold testing. The program may be executed by an execute input from a user, or executed in a process of setting a vibration intensity of each vibrator of a shoe-type device. The program may be, for example, an application installed in the terminal device 100, and the user may execute the application to measure a sensory threshold of the user that is to be applied to the shoe-type device. When the application is executed by processing circuitry of the terminal device 100, the processing circuitry 100 may be transformed to a special purpose processor that starts to perform the sensory threshold testing.

In operation 520, the terminal device 100 determines sensory threshold information of the user based on a choice input by the user that is received in a process of the sensory threshold testing. The terminal device 100 may determine a sensory threshold value of each of a left foot of the user and a right foot of the user. For example, the terminal device 100 may determine, as a result of the sensory threshold testing, a sensory threshold value for each of a left forefoot of the user, a left rearfoot of the user, a right forefoot of the user, and a right rearfoot of the user.

According to an example embodiment, the sensory threshold testing may include performing a first test and performing a second test. The first test may be performed to determine a rough sensory threshold value of a foot of the user, and the second test may be performed to obtain a final sensory threshold value of the user in a detailed way based on the rough sensory threshold value determined through the first test.

In the first test, the terminal device 100 may determine a sensory threshold value of a foot of the user based on a choice that is input by the user. According to an example embodiment, the terminal device 100 may generate a control signal for applying a test vibration to a current sole portion among a plurality of sole portions of the foot of the user, and transmit the generated control signal to the shoe-type device. The current sole portion may be one that is randomly selected from among the sole portions of the foot of the user.

The terminal device 100 may determine an intensity of the test vibration within a range from a minimum intensity to a maximum intensity. For example, when the minimum intensity of the test vibration is 1 and the maximum intensity of the test vibration is 100, the terminal device 100 may determine an intensity of the test vibration within a range from 1 to 100. For example, the terminal device 100 may determine an initial intensity of the test vibration to be 1.

In some example embodiments, the terminal device 100 may determine the initial intensity based on, parameters associated with the user. For example, the terminal device 100 may factor in one or more of a weight and age of the user or a thickness of a sock of the user to determine the initial intensity of the test vibration. The terminal device 100 may receive input from the user indicating a value of these parameters, or, alternatively, the terminal device 100 may measure values of some of these parameters, such as the weight of the user, using sensors in the shoe-type device 1. By customizing the initial intensity, the terminal device may increase the convenience of the user by reducing a length of time associated with the sensory threshold testing.

In this example, the terminal device may generate a control signal for applying the test vibration of the determined intensity to the foot of the user through a vibrator of the shoe-type device, and transmit the generated control signal to the shoe-type device. When the shoe-type device receives the control signal from the terminal device, the shoe-type device may generate the test vibration through a vibrator corresponding to the current sole portion.

However, when the terminal device 100 does not receive a correct input by the user for a sole portion from which the user senses the test vibration, the terminal device 100 may increase an intensity of the test vibration and generate a control signal for applying the test vibration of the increased intensity to the foot of the user through the vibrator, and transmit the generated control signal again to the shoe-type device. The terminal device 100 may gradually increase an intensity of the test vibration generated by the vibrator over time until the terminal device 100 receives the correct input by the user. For example, the terminal device 100 may increase an intensity of the test vibration by 5 points on the scale of 1 to 100 every 2 seconds from the initial intensity, which is 1.

In some example embodiments, when the terminal device 100 continually receives the incorrect input from the user, the terminal device 100 may determine whether the user has the shoe-type device 1 on their wrong feet. For example, the terminal device 100 may display a screen instructing the user to confirm that the right and left shoe-type device 1 are each on the correct feet of the user.

When the user senses a vibration through the shoe-type device, the user may input, to the terminal device 100, a choice of a sole portion of the foot from which the user senses the vibration. The terminal device 100 may then receive the choice input by the user for the sole portion among the sole portions of the foot of the user. When the terminal device 100 receives the choice input by the user, the terminal device may generate a control signal for suspending the generation of the test vibration, and transmit the generated control signal to the shoe-type device to control the shoe-type device not to generate the test vibration further.

The terminal device 100 may determine whether the current sole portion at which the test vibration is actually generated corresponds to the sole portion selected by the user corresponding to the input choice, and determine whether the user senses the test vibration correctly. When the current sole portion corresponds to the selected sole portion, the terminal device 100 may store information associated with the current sole portion and a most recent intensity of the test vibration generated by the vibrator corresponding to the current sole portion. Subsequently, the terminal device 100 may randomly select a sole portion for a next test from among the sole portions of the foot of the user, and perform repeatedly the foregoing process on the selected sole portion.

However, when the current sole portion does not correspond to the selected sole portion, the terminal device 100 may generate a control signal for applying again a test vibration to the current sole portion and transmit the generated control signal to the shoe-type device. When the shoe-type device receives the control signal, the shoe-type device may generate the test vibration through the vibrator corresponding to the current sole portion based on the received control signal. Here, an initial intensity of the test vibration to be applied to the current sole portion may be determined based on an intensity of the test vibration that is most recently applied to the current sole portion. For example, the initial intensity of the test vibration may be equal to the most recently applied intensity of the test vibration, and may increase gradually over time.

When a reference sensory threshold value is determined for each of the sole portions of the user through the first test, the second test may be determined. In the second test, the terminal device may determine a final sensory threshold value for the foot of the user based on the reference sensory threshold value determined through the first test.

In the second test, the terminal device may generate a control signal for applying a test vibration to a current sole portion among the sole portions of the foot of the user based on the reference sensory threshold value determined in the first test. The current sole portion may be one that is randomly selected from among the sole portions of the user. The terminal device may determine an intensity of the test vibration based on the reference sensory threshold value. The terminal device may generate a control signal for applying the test vibration of the determined intensity to the foot of the user through a vibrator of the shoe-type device, and transmit the generated control signal to the shoe-type device.

When the terminal device 100 does not receive a choice input by the user for a sole portion from which the user senses the test vibration, the terminal device 100 may increase an intensity of the test vibration and generate a control signal for applying the test vibration of the increased intensity to the foot of the user through the vibrator, and then transmit again the generated control signal to the shoe-type device. The terminal device 100 may gradually increase an intensity of the test vibration generated by the vibrator over time until the terminal device receives a choice input by the user. Here, a value of a change in the vibration intensity applied in the second test over time may be less than a value of a change in vibration intensity applied in the first test over time. For example, the intensity of the test vibration may increase by 1 on the scale of 1 to 100 every 2 seconds starting from an intensity that is obtained by subtracting a certain value from an intensity of the test vibration corresponding to the reference sensory threshold value.

When the user senses a vibration through the shoe-type device, the user may input, to the terminal device 100, a choice of a sole portion of the foot from which the user senses the vibration. The terminal device 100 may then receive the choice input by the user for the sole portion among the sole portions of the foot of the user. When the terminal device 100 receives the choice input by the user, the terminal device 100 may generate a control signal for suspending the generation of the test vibration, and transmit the generated control signal to the shoe-type device to control the shoe-type device not to generate the test vibration further.

The terminal device 100 may determine whether the current sole portion at which the test vibration is actually generated corresponds to the sole portion selected by the user corresponding to the input choice, and determine whether the user senses the test vibration correctly. When the current sole portion corresponds to the selected sole portion, the terminal device 100 may store information associated with the current sole portion and a most recent intensity of the test vibration generated by the vibrator corresponding to the current sole portion. Subsequently, the terminal device 100 may randomly select a sole portion for a next test from among the sole portions of the foot of the user, and perform repeatedly the foregoing process on the selected sole portion.

However, when the current sole portion does not correspond to the selected sole portion, the terminal device 100 may generate a control signal for applying again a test vibration to the current sole portion and transmit the generated control signal to the shoe-type device. When the shoe-type device 1 receives the control signal, the shoe-type device 1 may generate the test vibration through the vibrator corresponding to the current sole portion based on the received control signal. Here, an initial intensity of the test vibration to be applied to the current sole portion may be determined based on an intensity of the test vibration that is most recently applied to the current sole portion. For example, the initial intensity of the test vibration may be equal to the most recently applied intensity of the test vibration, and may increase gradually over time.

According to an example embodiment, the terminal device 100 may obtain a plurality of sensory threshold values for each of the sole portions by repeatedly performing the foregoing process of the second test, and determine the final sensory threshold value for each of the sole portions based on at least a portion of the plurality of obtained sensory threshold values. For example, when the terminal device 100 determines five (5) sensory threshold values for a left forefoot of the user through the second test, the terminal device may determine, to be a final sensory threshold value corresponding to the left forefoot of the user, an average value of three (3) sensory threshold values that are lowest among the five sensory threshold values. The terminal device may determine a final sensory threshold value for another sole portion of the user in the same way as described in the foregoing.

In operation 530, the terminal device 100 transmits the sensory threshold information determined in operation 520 to the shoe-type device 1. For example, the terminal device 100 may transmit the sensory threshold information to the shoe-type device 1 through Bluetooth communication. The shoe-type device 1 may then determine an optimal intensity of a vibration to be generated through each vibrator of the shoe-type device 1 based on the received sensory threshold information. For example, the shoe-type device 1 may determine an intensity of a vibration to be generated by a vibrator corresponding to a left forefoot of the user to be an intensity corresponding to 90% of a final sensory threshold value determined for the left forefoot of the user. The shoe-type device 1 may also determine an intensity of a vibration to be generated by a vibrator corresponding to another sole portion of the user to be an intensity corresponding to 90% of a final sensory threshold value determined for the other sole portion of the user.

FIGS. 6 through 9 are diagrams illustrating an example of a series of operations to be performed for sensory threshold testing according to at least one example embodiment.

In the example to be described hereinafter with reference to FIGS. 6 through 9, a sensory threshold of each of a left forefoot, a left rearfoot, a right forefoot, and a right rearfoot of a user may be individually measured. However, examples are not limited to the illustrated example, and a sensory threshold test may be performed on various sole portions of feet of the user. Alternatively, the sensory threshold test may be performed on a lower number of sole portions of the feet of the user. According to an example embodiment, the sensory threshold test may be performed while the user is sitting with a shoe-type device on. The sensory threshold test may be performed in a way that the user selects a location or a sole portion at which the user senses that a vibration is generated.

Figure 6:
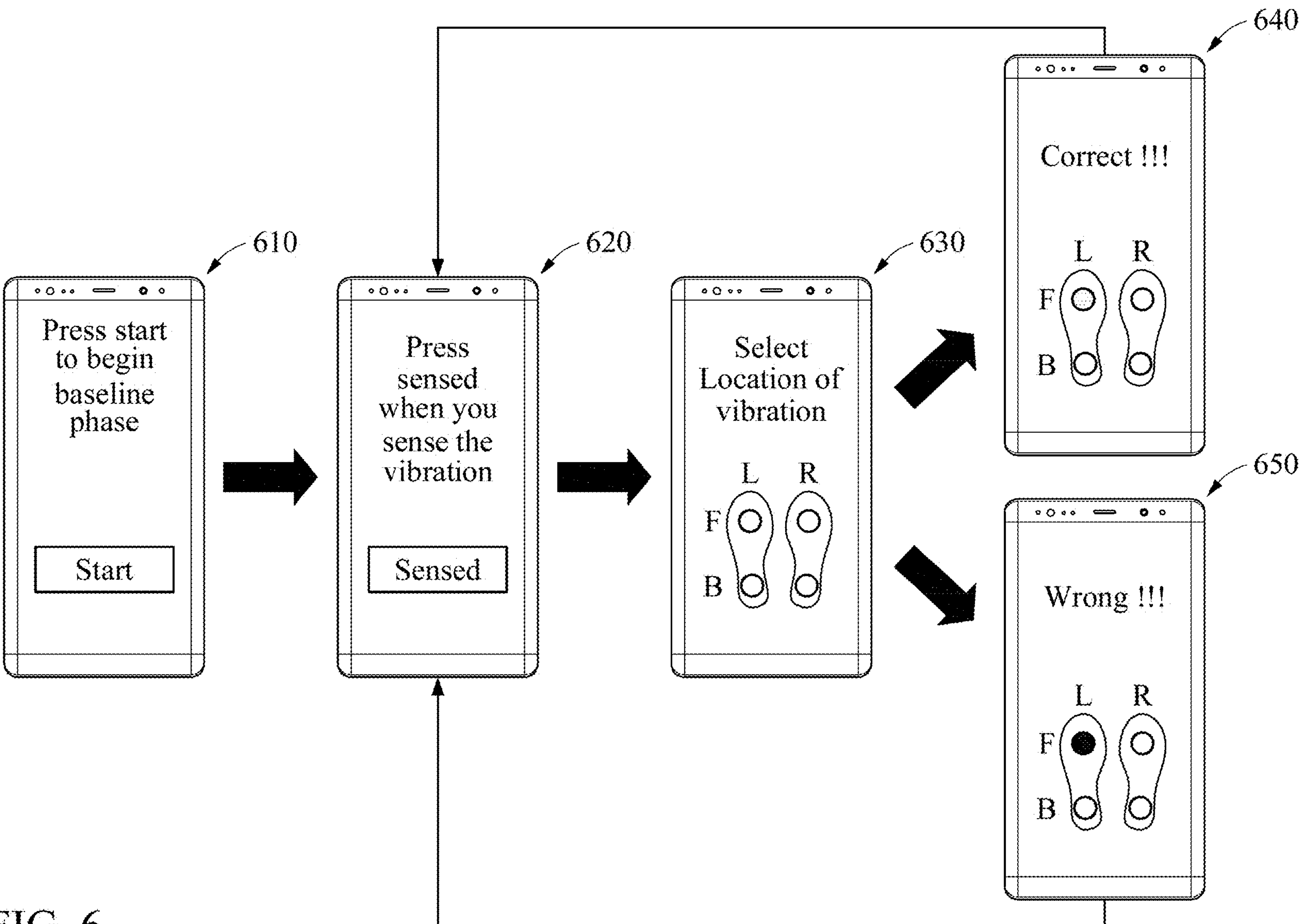
FIGS. 6 through 9 are diagrams illustrating an example of a series of operations to be performed for sensory threshold testing according to at least one example embodiment.

Referring to FIG. 6, a process for determining a reference sensory threshold value is performed.

In operation 610, the terminal device 100 may output an interface screen for asking the user whether to start a first sensory threshold test, for example, a baseline phase. When the user inputs a choice to start the first sensory threshold test, the first sensory threshold test may be performed. According to an example embodiment, the terminal device 100 may randomly select a current sole portion to which a test vibration is to be applied from among a plurality of sole portions of a foot of the user, and determine an initial intensity of the test vibration to be generated at the selected current sole portion. The shoe-type device 1 may receive information associated with the current sole portion selected by the terminal device 100 and the initial intensity of the test vibration, and generate the test vibration of the initial intensity through a vibrator corresponding to the current sole portion based on the received information.

In operation 620, the terminal device 100 may output an interface screen for receiving a choice input by the user for whether the user senses a vibration on the foot of the user. Until the input choice is received from the user, the terminal device 100 may gradually increase an intensity of the test vibration that is generated by the shoe-type device 1 over time. For example, the intensity of the test vibration generated in the current sole portion may increase by 5 on a scale of 1 to 100 every 2 seconds starting from 1. When the input choice is received from the user, the terminal device 100 may transmit a control signal for suspending the generation of the test vibration to the shoe-type device 1.

In operation 630, the terminal device 100 may output an interface screen for verifying a sole portion from which the user senses the test vibration among a plurality of sole portions of the foot of the user. When the user inputs a choice of a certain sole portion from which the user senses the test vibration, the terminal device 100 may determine whether the current sole portion in which the test vibration is actually generated corresponds to the sole portion selected by the user corresponding to the input choice.

In operation 640, the terminal device 100 may output a result screen indicating that the choice input by the user is correct, when the current sole portion corresponds to the selected sole portion. The terminal device 100 may store information associated with the current sole portion and a most recent intensity of the test vibration generated by the vibrator corresponding to the current sole portion. Subsequently, the terminal device 100 may randomly select a sole portion for a next test from among the sole portions of the foot of the user, and perform repeatedly the foregoing process of the sensory threshold test. According to an example, the sole portion for the next test may be determined from among remaining sole portions excluding the current sole portion.

In operation 650, the terminal device 100 may output a result screen indicating that the choice input by the user is incorrect, when the current sole portion does not correspond to the selected sole portion. The terminal device 100 may generate a control signal for applying again a test vibration to the current sole portion, and transmit the generated control signal to the shoe-type device 1. The shoe-type device 1 may then generate the test vibration by the vibrator corresponding to the current sole portion based on the control signal. Here, an initial intensity of the test vibration to be applied to the current sole portion may increase by 5 on a scale of 1 to 100 every 2 seconds starting from the intensity most recently applied to the current sole portion.

A sensory threshold value determined for each of the sole portions of the foot of the user through the foregoing operations may correspond to a reference sensory threshold value. For example, when a plurality of sensory threshold values is determined for a sole portion, the terminal device 100 may determine a reference sensory threshold value for the sole portion to be an average value of a preset number of sensory threshold values in an order starting from the smallest sensory threshold value among the determined sensory threshold values, or the smallest sensory threshold value among the determined sensory threshold values.

After a reference sensory threshold value is determined for each sole portion of the user, the terminal device 100 may perform a test to determine a more detailed sensory threshold value as described hereinafter with reference to FIG. 7.

Figure 7:
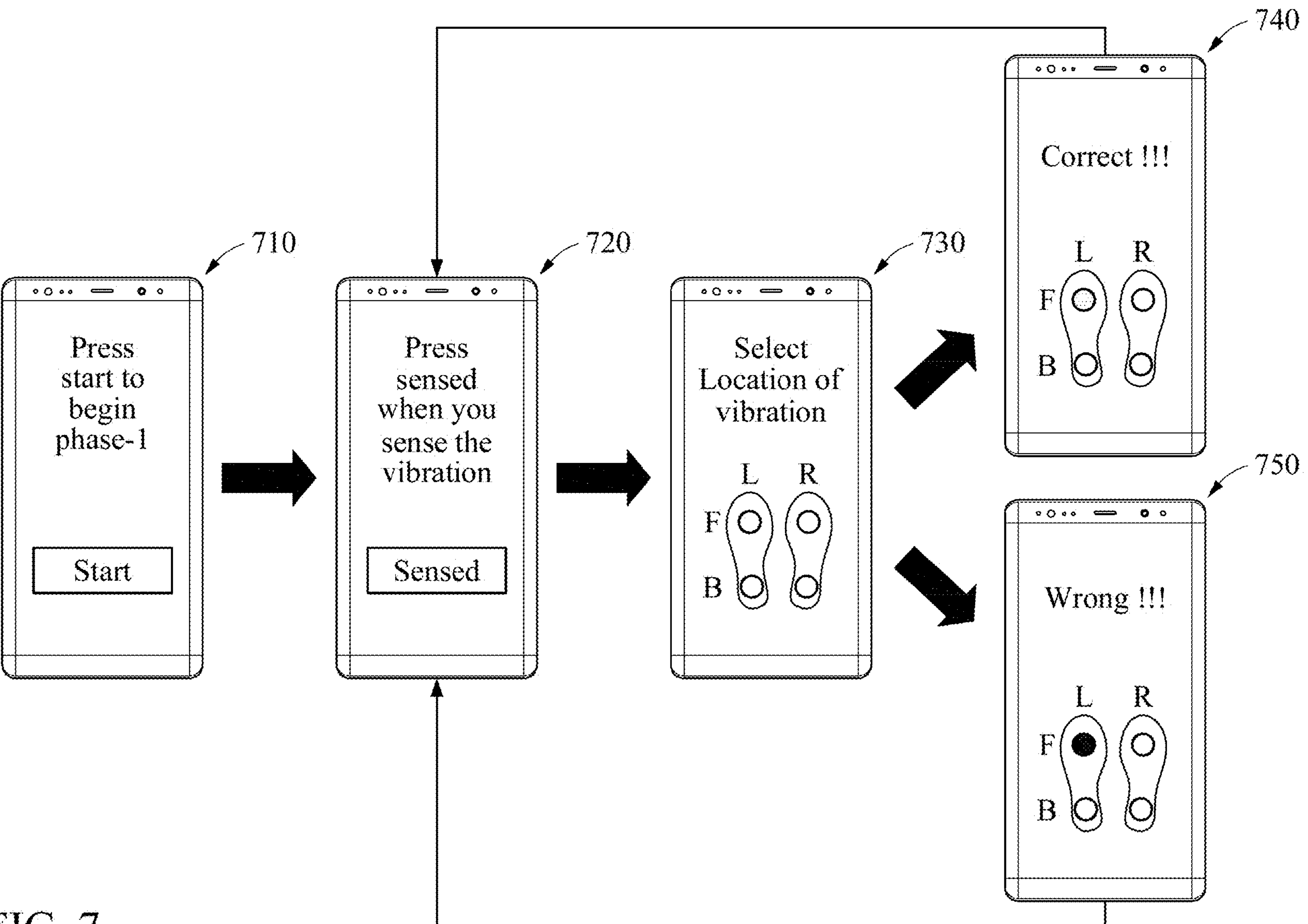

Referring to FIG. 7, in operation 710, the terminal device 100 outputs an interface screen for asking the user whether to start a second sensory threshold test, for example, phase-1. When the user inputs a choice to start the second sensory threshold test through the interface screen, the terminal device 100 may start the second sensory threshold test.

According to an example embodiment, the terminal device 100 may randomly select a current sole portion to which a test vibration is to be applied from among a plurality of sole portions of a foot of the user, and determine an initial intensity of the test vibration to be generated in the selected current sole portion. Here, the initial intensity of the test vibration to be applied to the current sole portion may be determined based on the reference sensory threshold value determined for the current sole portion in the first sensory threshold test. For example, when the reference sensory threshold value determined for the current sole portion in the first sensory threshold test is 20 on a scale of 1 to 100, the initial intensity of the test vibration to be generated in the current sole portion in the second sensory threshold test may be determined to be a value less than 20, for example, 10 which is obtained by applying −10 to 20.

The terminal device 100 may generate a control signal for applying the test vibration of the determined initial intensity to the foot of the user through a vibrator of the shoe-type device 1, and transmit the generated control signal to the shoe-type device 1. The shoe-type device 1 may receive, from the terminal device 100, information associated with the current sole portion selected by the terminal device 100 and the initial intensity of the test vibration, and generate the test vibration of the initial intensity by the vibrator corresponding to the current sole portion based on the received information.

In operation 720, the terminal device 100 may output an interface screen for receiving a choice input by the user for whether the user senses a vibration on the foot of the user. Until the input choice is received from the user, an intensity of the test vibration generated by the shoe-type device may gradually increase over time. A value of a change in vibration intensity over time in the second sensory threshold test may be less than a value of a change in vibration intensity over time in the first sensory threshold test. For example, an intensity of a vibration may increase by 1 out of a scale of 1 to 100 every 2 seconds starting from an initial intensity of the vibration.

When the terminal device 100 receives the input choice from the user, the terminal device 100 may transmit a control signal for suspending the generation of the test vibration to the shoe-type device 1.

In operation 730, the terminal device 100 may output an interface screen for verifying a sole portion from which the user senses the test vibration among the sole portions of the foot of the user. When the user inputs a choice of a certain sole portion from which the user senses the test vibration among the sole portions of the foot of the user, the terminal device 100 may determine whether the current sole portion in which the test vibration is actually generated corresponds to the sole portion selected by the user corresponding to the input choice.

In operation 740, when the current sole portion corresponds to the selected sole portion, a result screen indicating that the choice input by the user is correct is output. The terminal device 100 may store information associated with the current sole portion and a most recent intensity of the test vibration generated by the vibrator corresponding to the current sole portion. Subsequently, the terminal device 100 may randomly select a sole portion for a next test from among the sole portions of the foot of the user, and perform repeatedly the foregoing operations on the selected sole portion. According to an example, the sole portion for the next test may be determined from among remaining sole portions excluding the current sole portion.

In operation 750, when the current sole portion does not correspond to the selected sole portion, the terminal device 100 may output a result screen indicating that the choice input by the user is incorrect. The terminal device 100 may generate a control signal for applying again a test vibration to the current sole portion, and transmit the generated control signal to the shoe-type device 1. The shoe-type device 1 may generate the test vibration through the vibrator corresponding to the current sole portion based on the received control signal. Here, an initial intensity of the test vibration to be applied to the current sole portion may increase by 1 on a scale of 1 to 100 every 2 seconds starting from an intensity of the test vibration that is most recently applied to the current sole portion.

Through the foregoing operations, a sensory threshold value may be determined for each of the sole portions of the user. According to an example embodiment, the terminal device 100 may perform a further test to measure a more detailed sensory threshold value of each of the sole portions of the user. For example, a third sensory threshold test, for example, phase-2, may be further performed as described hereinafter with reference to FIG. 8.

Figure 8:
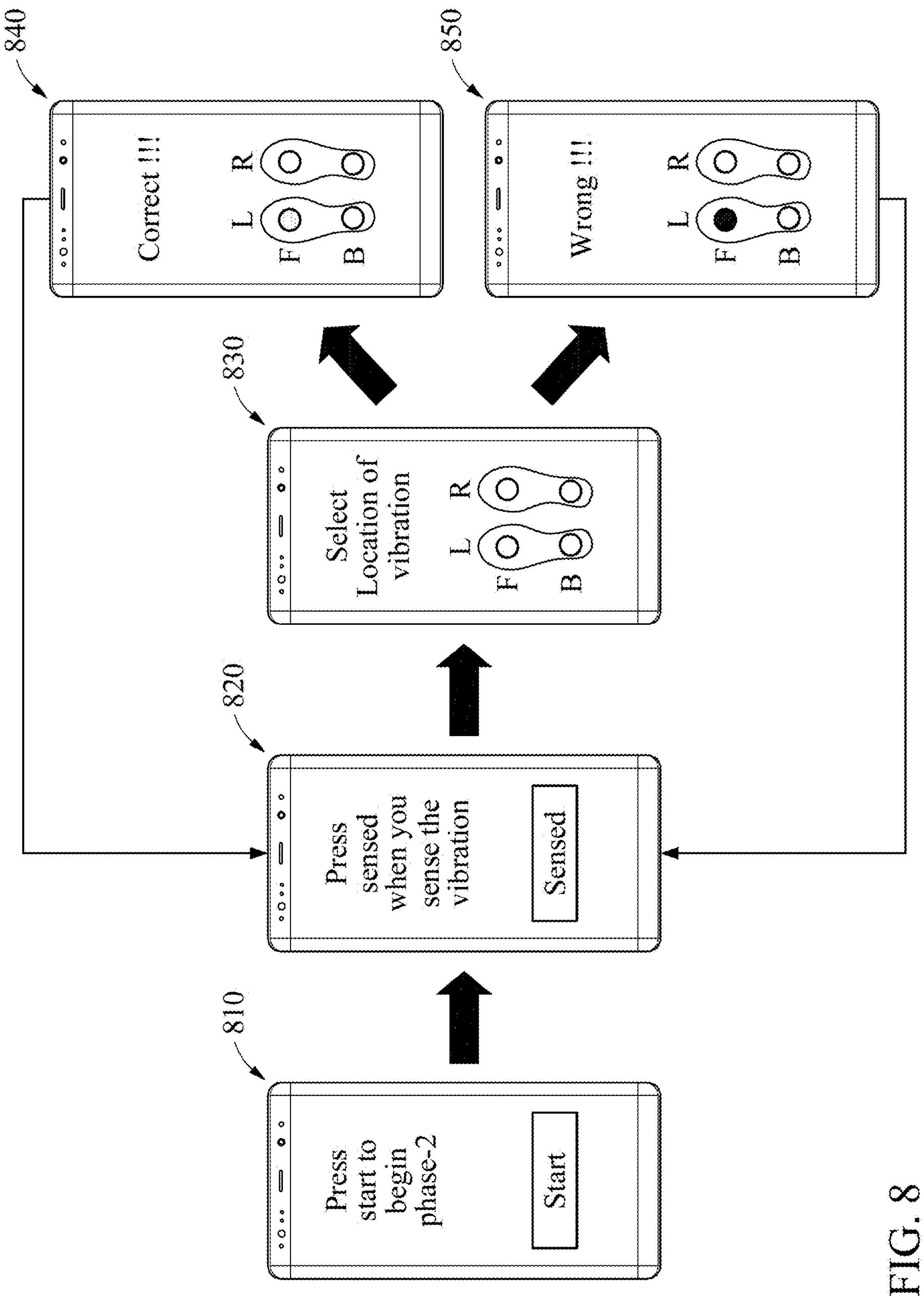

Referring to FIG. 8, in operation 810, an initial intensity of a test vibration to be applied to a current sole portion of the user is determined based on a sensory threshold value determined for the current sole portion in the second sensory threshold test. For example, when a reference sensory threshold value determined for the current sole portion in the second sensory threshold test is 18 on a scale of 1 to 100, the initial intensity of the test vibration to be generated in the current sole portion in the third sensory threshold test may be determined to be less than 18, for example, 13 obtained by applying −5 to 18. In the third sensory threshold test, an adjustment value that is less than an adjustment value (e.g., −10) applied to determine the initial intensity of the test vibration in the second sensory threshold test may be used. In the third sensory threshold test, except the determining of the initial intensity of the test vibration as described in the foregoing, operations 810, 820, 830, 840, and 850 may respectively correspond to operations 710, 720, 730, 740, and 750 described above with reference to FIG. 7.

According to an example, the terminal device 100 may obtain a plurality of sensory threshold values for each of the sole portions of the foot of the user by performing repeatedly the third sensory threshold test. The terminal device 100 may determine a final sensory threshold value corresponding to each of the sole portions of the foot of the user based on the obtained sensory threshold values. For example, when five sensory threshold values are determined for a left forefoot of the user through the third sensory threshold test, a final sensory threshold value corresponding to the left forefoot of the user may be determined to be an average value of three sensory threshold values in an order starting from the smallest sensory threshold value among the five sensory threshold values.

Figure 9:
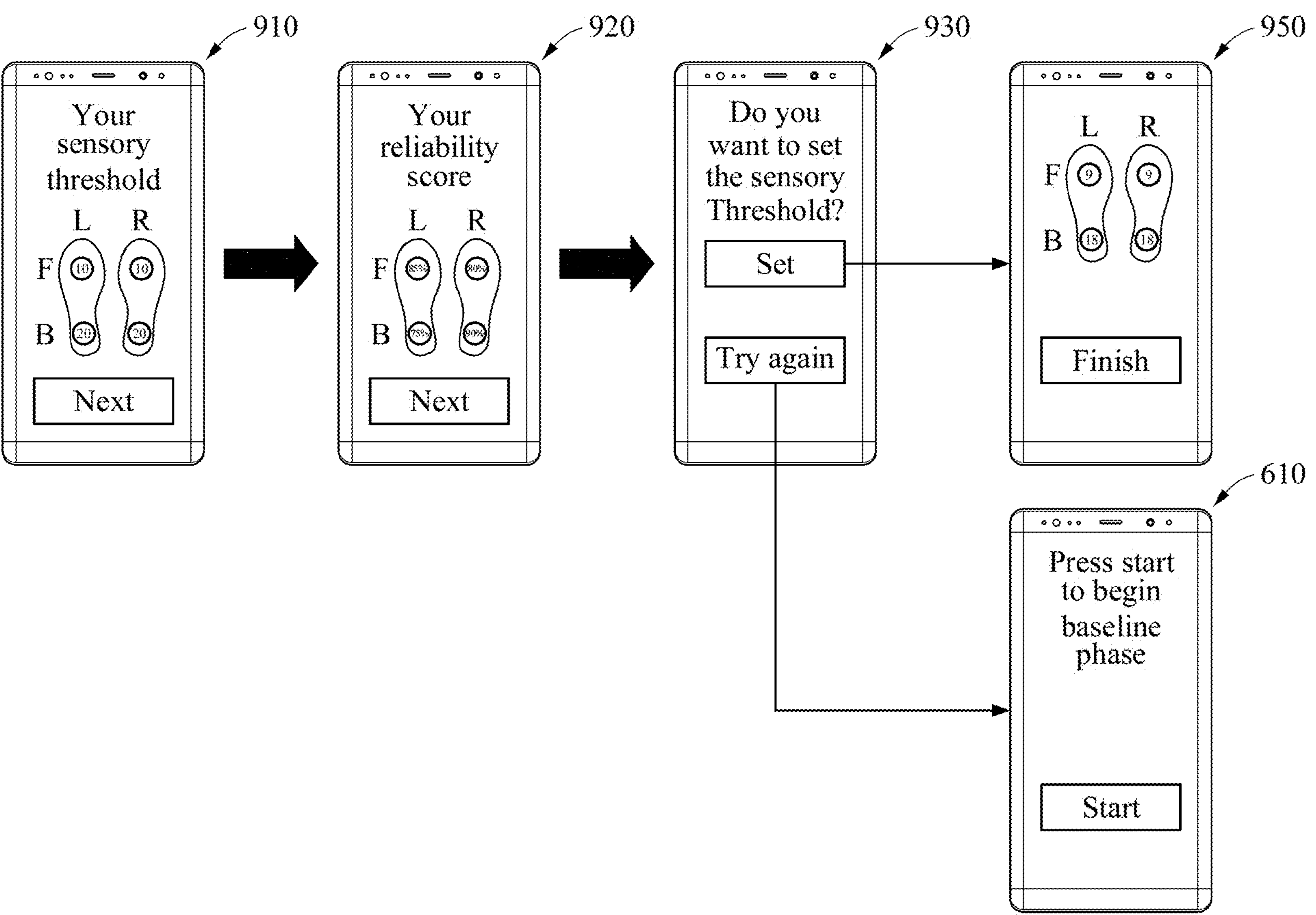

FIG. 9 illustrates an example of providing a sensory threshold test result.

Referring to FIG. 9, in operation 910, the terminal device 100 may determine a final sensory threshold value for each of sole portions of a foot of the user.

In operation 920, in some example embodiments, the terminal device 100 may provide a reliability rating of the final sensory threshold value. For example, the terminal device 100 may calculate an intraclass correlation coefficient (ICC) based on sensory threshold values obtained through a plurality of measurements, and determine a reliability of a final sensory threshold value based on the calculated ICC.

In operation 930, the terminal deice 100 may output an interface screen for asking the user whether to apply the determined final sensory threshold value to the shoe-type device 1.

In operation 950, when the user inputs a choice to apply the final sensory threshold value to the shoe-type device 1, the terminal device 100 may generate sensory threshold information based on the final sensory threshold value of each of the sole portions of the foot of the user and transmit the generated sensory threshold information to the shoe-type device 1. The shoe-type device 1 may then determine an optimal intensity of a vibration to be generated through each vibrator based on the received sensory threshold information. For example, the shoe-type device 1 may determine the optimal intensity of the vibration to be an intensity corresponding to 90% of the final sensory threshold value.

When the user selects to restart the sensory threshold test by inputting a corresponding choice to the interface screen output in operation 930, the terminal device 1 may return to operation 610 and the sensory threshold test may restart.

Through the sensory threshold test as described above, it is possible to individually measure a sensory threshold of each of a left foot and a right foot of a user, and more accurately determine an optimal vibration intensity corresponding to each sole portion of the left foot and the right foot.

Figure 10:
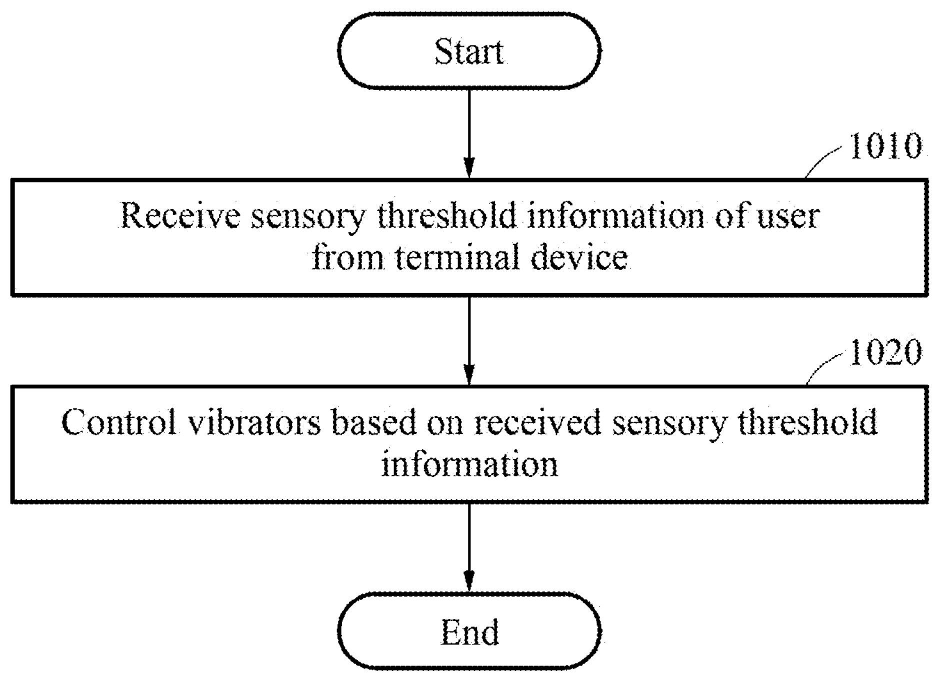
FIG. 10 is a flowchart illustrating an example of a method of controlling a shoe-type device according to at least one example embodiment.

FIG. 10 is a flowchart illustrating an example of a method of controlling a shoe-type device 1 according to at least one example embodiment. The method of controlling a shoe-type device 1 to be described hereinafter with reference to FIG. 10 may be performed by the control device 20 of the shoe-type device 1.

Referring to FIG. 10, in operation 1010, the control device 20 receives, from the terminal device 100, sensory threshold information of a user that is determined through the sensory threshold testing, as described above in reference to FIGS. 4-9. The control device 20 may receive the sensory threshold information from the terminal device 100 through wireless communication, for example, Bluetooth communication. The sensory threshold testing may include performing the first test, as described with reference to FIG. 6, to determine a reference sensory threshold value for a foot of the user based on a choice input by the user, and performing one or more second tests, as described with reference to FIGS. 7 and 8, to determine a final sensory threshold value, as described with reference to FIG. 9, for the foot of the user based on the determined reference sensory threshold value. The sensory threshold information determined as described in the foregoing may include a final sensory threshold value of each of a left forefoot of the user, a left rearfoot of the user, a right forefoot of the user, and a right rearfoot of the user.

In operation 1020, the control device 20 controls vibrators included in the shoe-type device 1 based on the received sensory threshold information. The control device 20 may determine an optimal intensity of a vibration to be generated through each of the vibrators of the shoe-type device 1 based on the sensory threshold information. For example, the control device 20 may control a vibrator corresponding to the left forefoot of the user to generate a vibration of an intensity corresponding to 90% of a final sensory threshold value determined for the left forefoot of the user. In addition, the control device 20 may control another vibrator corresponding to another sole portion of a foot of the user to generate a vibration of an intensity corresponding to 90% of a final sensory threshold value determined for the other sole portion of the foot of the user. An optimal intensity of a vibration to be generated by a vibrator may need to be less than an intensity corresponding to a final sensory threshold value, and may not necessarily be 90% of the final sensory threshold value.

In some example embodiments, the terminal device 100 (or, alternatively, the control device 20) may control the plurality of vibrators 133*a*, 133*b* or 433*a*, 433*b* to generate the desired intensity of vibration where the vibration has a frequency that changes (e.g. randomly) such that at least a portion of the vibration resonates along with an external stimulus with a baseline of the intensity being determined based on the final sensory threshold value.

In some example embodiments, the terminal device 100 (or, alternatively, the control device 20) may estimate a posture of the user by measuring foot pressure of the user, and selectively activate the plurality of vibrators 133*a*, 133*b* or 433*a*, 433*b* only when the posture of the user is a walking posture and/or a standing posture. Therefore, the terminal device 100 (or, alternatively, the control device 20) may improve the functioning of the shoe-type device 1 itself by reducing power consumption of the battery and/or increasing comfortableness that may be experienced by the user.

In some example embodiments, the terminal device 100 (or, alternatively, the control device 20) may measure a pressure applied to the sole of the user using the pressure sensor 143*b*, and detect a center of pressure (COP) therefrom. The terminal device 100 (or, alternatively, the control device 20) may be in communication with a walking assistance apparatus worn by the user, and instruct the walking assistance apparatus to output an assistance force that rebalances pressures applied to the sole of the user based on the center of pressure (COP).

Figure 11:
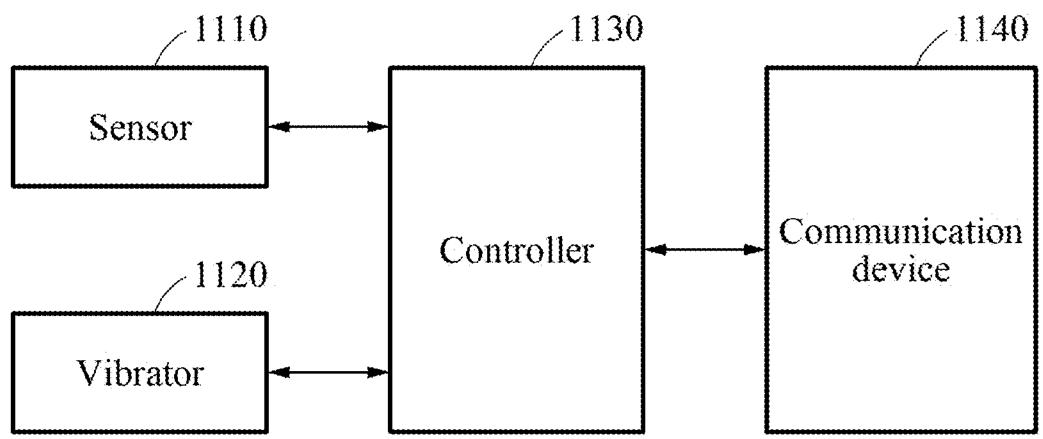
FIG. 11 is a diagram illustrating an example of a shoe-type device according to at least one example embodiment.

FIG. 11 is a diagram illustrating an example of a shoe-type device according to at least one example embodiment.

Referring to FIG. 11, a shoe-type device 1100 includes a sensor 1110, a vibrator 1120, a controller 1130, and a communication device 1140.

The sensor 1110 may sense an internal or external environment of the shoe-type device 1100 and include, for example, a pressure sensor and a motion sensor. Here, the sensor 1110 may be provided as a plurality of sensors.

The vibrator 1120 may generate a vibration under the control of the controller 1130. According to an example embodiment, the vibrator 1120 may generate a vibration of an intensity less than a sensory threshold of a user wearing the shoe-type device 1100, and the generated vibration may trigger stochastic resonance. Here, the vibrator 1120 may be provided as a plurality of vibrators.

The controller 1130 may control each component of the shoe-type device 1100 and include at least one processor.

The communication device 1140 may communicate with an external device through wired or wireless communication. For example, the communication device 1140 may include a wireless transmission antenna and a wireless reception antenna, and communicate with a terminal device through wireless communication, for example, Bluetooth communication. According to an example embodiment, the communication device 1140 may receive, from the terminal device, sensory threshold information of the user that is determined through sensory threshold testing. The sensory threshold information may include, for example, a sensory threshold value of each of a left forefoot of the user, a left rearfoot of the user, a right forefoot of the user, and a right rearfoot of the user that is determined through the sensory threshold testing.

The controller 1130 may control the vibrator 1120 based on the received sensory threshold information. When the vibrator 110 includes a plurality of vibrators, the controller 1130 may determine an optimal intensity of a vibration to be generated by each of the vibrators disposed in different portions of the shoe-type device 1100 based on the sensory threshold information. For example, the controller 1130 may set the optimal intensity of the vibration to be generated through each of the vibrators to be less than an intensity corresponding to a final sensory threshold value determined for each of sole portions of feet of the user. In addition, the controller 1130 may control one or more, or all, of the operations and methods described above in relation to a shoe-type device with reference to FIGS. 1 through 10.

Figure 12:
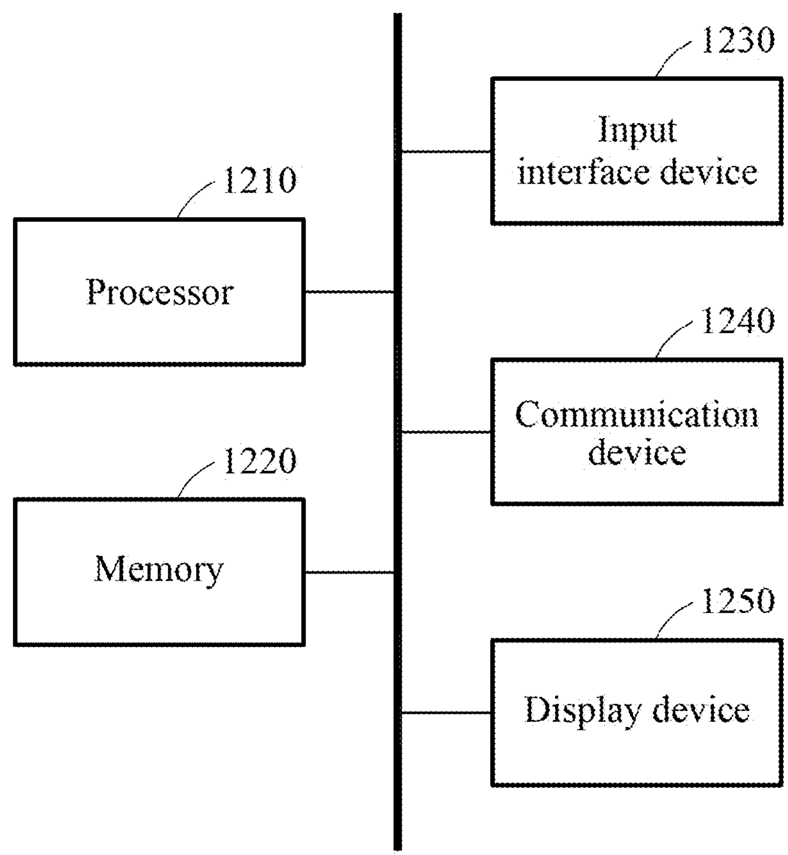
FIG. 12 is a diagram illustrating an example of a terminal device according to at least one example embodiment.

FIG. 12 is a diagram illustrating an example of a terminal device according to at least one example embodiment.

Referring to FIG. 12, a terminal device 1200 includes a processor 1210, a memory 1220, an input interface device 1230, a communication device 1240, and a display device 1250. Each of such components of the terminal device 1200 may exchange data and/or information with another component of the terminal device 1200 through a communication bus.

The memory 1220 may store data and/or information. The memory 1220 may include a computer-readable storage medium or a computer-readable storage device. For example, the memory 1220 may include a random-access memory (RAM), a dynamic RAM (DRAM), a static RAM (SRAM), or other types of non-volatile memories that are well-known in the field of technology. The memory 1220 may store instructions to be executed by the processor 1210, and related information while a program for sensory threshold testing is being executed by the terminal device 1200.

The input interface device 1230 may receive an input from a user, as a non-limiting example, a tactile input, a video input, an audio input, and a touch input. The input interface device 1230 may detect the input from the user through, for example, a keyboard, a mouse, a touchscreen, a microphone, and the like, and include other devices configured to transfer the detected input to the terminal device 1200. For example, the input interface device 1230 may receive a choice input by the user in a process of the sensory threshold testing.

The communication device 1240 may communicate with an external device through a wired or wireless network. The communication device 1240 may communicate with the external device through wired communication, or wireless communication such as, for example, WiFi, third generation (3G) communication, and long-term evolution (LTE) communication. According to an example embodiment, the communication device 1240 may wirelessly communicate with a shoe-type device through Bluetooth communication and transmit, to the shoe-type device, sensory threshold information and a control signal for controlling the shoe-type device.

The display device 1250 may provide the user with an output of the terminal device 1200 in a visual way. The display device 1250 may include, as non-limiting example, a liquid crystal display (LCD), a light-emitting diode (LED) display, a touchscreen, and other devices configured to provide the user with a visual output. According to an example embodiment, the display device 1250 may display a screen for the program for the sensory threshold testing.

The processor 1210 may control the terminal device 1200, and perform functions and execute instructions in the terminal device 1200. For example, the processor 1210 may process instructions stored in the memory 1220. The processor 1210 may perform one or more, or all, of the operations or methods described above in relation to a terminal device with reference to FIGS. 1 through 11. According to an example embodiment, the processor 1210 may execute a program for sensory threshold testing, and determine sensory threshold information of a user based on a choice input by the user that is received in a process of the sensory threshold testing. In the process of the sensory threshold testing, the processor 1210 may determine the sensory threshold information by performing a first test to determine a reference sensory threshold value for a foot of the user based on a corresponding choice input by the user, and performing at least one second test to determine a final sensory threshold value for the foot of the user based on the determined reference sensory threshold value. The processor 1210 may control the communication device 1240 to transmit the determined sensory threshold information to the shoe-type device 1.

The units and/or modules described herein may be implemented using hardware components and software components.

For example, the control device 20 associated with the shoe-type device 1 and the processor 1210 associated with the terminal device 100 may each include processing circuitry including, but is not limited to, a central processing unit (CPU), an arithmetic logic unit (ALU), a digital signal processor, a microcomputer, a field programmable gate array (FPGA), a programmable logic unit, a microprocessor, application-specific integrated circuit (ASIC), etc. The processing circuitry may be special purpose processing circuitry that configures the terminal device 100 to measure a sensory threshold of a different portions of the plantar sole of each foot of the user using only the terminal device 100 and the shoe-type device 1 without for example, requiring a medical professional, and customize the intensity of the stimulus provided by corresponding ones of the plurality of vibrators associated with each of the shoe-type device 1 based on the measured sensory thresholds. Therefore, the system may improve the functioning of the shoe-type device 1 by determining a desired (or, alternatively an minimum) level of the stochastic resonance provided to the user while reducing unnecessary battery consumption and/or inconvenience felt by the user due to excess stochastic resonance.

For example, the hardware components may include microphones, amplifiers, band-pass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, apiece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A method of setting sensory threshold information for a wearable device included in a shoe worn by a user, the method comprising:

controlling a graphical user interface (GUI) of terminal device to display an interface screen requesting user input from the user to begin a sensory threshold test;

performing the sensory threshold test on the user in response to receipt of the user input to begin the sensory threshold test, the performing the sensory threshold test including, performing a first test by instructing the wearable device to provide a stimulus to the user while controlling the GUI such that an intensity of the stimulus provided to the user increases while the GUI displays an instruction on the interface screen requesting the user receiving the stimulus to provide a selection input indicating when the user senses the stimulus provided by the wearable device during the first test, and performing a second test after the first test by instructing the wearable device to provide the stimulus to the user while controlling the GUI such that the intensity of the stimulus provided to the user during the second test increases at a different rate from the intensity of the stimulus provided to the user during the first test while the GUI displays an instruction on the interface screen requesting the user provide a second selection input indicating when the user senses the stimulus provided by the wearable device during the second test, wherein a second rate of change in the intensity of the stimulus applied to the foot of the user during the second test is less than a first rate of change in the intensity of the stimulus applied to the foot of the user during the first test;

determining the sensory threshold information of the user based on the intensity of the stimulus provided to the user at a time when the second selection input was received from the user during the second test; and transmitting the sensory threshold information to the wearable device.

2. The method of claim 1, wherein the determining of the sensory threshold information comprises:

determining a sensory threshold value for each of a left foot and a right foot of the user.

3. The method of claim 2, wherein the determining of the sensory threshold information comprises:

determining the sensory threshold value for each of a forefoot and a rearfoot of the left foot of the user, and a forefoot and a rear foot of the right foot of the user.

4. The method of claim 1, wherein a reference sensory threshold value is set to a level of the intensity of the stimulus provided to the user at the time when the selection input was received from the user during the first test, and a final sensory threshold value for a foot of the user is set based on a level of the intensity of the stimulus provided to the user at the time when the second selection input was received from the user during the second test.

5. The method of claim 4, wherein the performing of the first test comprises:

transmitting, to the wearable device, a control signal instructing the wearable device to apply a test vibration to a current sole portion among a plurality of sole portions of the foot of the user;

receiving an input from the user indicating a selected one of the plurality of sole portions; and determining whether the current sole portion corresponds to the selected one of the plurality of sole portions.

6. The method of claim 5, further comprising:

randomly selecting a next sole portion to receive the test vibration from among the plurality of sole portions, in response to the current sole portion corresponding to the selected one of the plurality of sole portions.

7. The method of claim 5, further comprising:

transmitting, to the wearable device, a control signal instructing the wearable device to again apply the test vibration to the current sole portion, in response to the current sole portion not corresponding to the selected one of the plurality of sole portions.

8. The method of claim 7, wherein an initial intensity of the test vibration applied to the current sole portion is based on an intensity of the test vibration most recently applied to the current sole portion.

9. The method of claim 4, wherein the performing the second test comprises:

repeatedly performing the second test to obtain a plurality of sensory threshold values; and determining the final sensory threshold value based on the plurality of sensory threshold values.

10. The method of claim 4, wherein the performing of the first test comprises:

determining an intensity of a test vibration in a range between a minimum intensity and a maximum intensity; and transmitting, to the wearable device, a control signal instructing the wearable device to apply the test vibration of the determined intensity to the foot of the user through a vibrator of the wearable device.

11. The method of claim 10, wherein the determining of the intensity of the test vibration comprises:

increasing the intensity of the test vibration, in response to not receiving the input from the user.

12. The method of claim 4, wherein the performing of the second test comprises:

transmitting, to the wearable device, a control signal instructing the wearable device to apply a test vibration to a current sole portion among a plurality of sole portions of the foot of the user based on the reference sensory threshold value;

receiving an input from the user indicating a selected one of the plurality of sole portions; and determining whether the current sole portion corresponds to the selected one of the plurality of sole portions.

13. The method of claim 12, further comprising:

randomly selecting a next sole portion to receive the test vibration from among the plurality of sole portions, in response to the current sole portion corresponding to the selected one of the plurality of sole portions.

14. The method of claim 12, further comprising:

transmitting, to the wearable device, a control signal instructing the wearable device to again apply the test vibration to the current sole portion, in response to the current sole portion not corresponding to the selected one of the plurality of sole portions.

15. The method of claim 14, wherein an initial intensity of the test vibration applied to the current sole portion is based on an intensity of the test vibration most recently applied to the current sole portion.

16. The method of claim 4, wherein the performing of the second test comprises:

determining an intensity of a test vibration based on the reference sensory threshold value; and transmitting, to the wearable device, a control signal instructing the wearable device to apply the test vibration of the determined intensity to the foot of the user through a vibrator of the wearable device.

17. The method of claim 16, wherein the determining of the intensity of the test vibration comprises:

increasing the intensity of the test vibration, in response to not receiving the input from the user.

18. The method of claim 1, wherein the transmitting of the sensory threshold information comprises:

transmitting the sensory threshold information to the wearable device via Bluetooth communication.

19. A method of operating a wearable device included in a shoe worn by a user to provide a stimulus to the user, the wearable device configured to communicate with a terminal device, the terminal device including a graphical user interface (GUI), the method comprising:

receiving, from the terminal device, sensory threshold information of the user, the sensory threshold information determined via a sensory threshold test, the sensory threshold test including, a first test in which the wearable device provides a stimulus to the user while the terminal devices controls the GUI such that an intensity of the stimulus provided to the user increases while the GUI displays an instruction on an interface screen requesting the user receiving the stimulus to provide a selection input indicating when the user senses the stimulus provided by the wearable device during the first test to determine a reference sensory threshold value for a foot of the user, and a second test performed after the first test in which the wearable device provides the stimulus to the user while controlling the GUI such that the intensity of the stimulus provided to the user during the second test increases at a different rate from the intensity of the stimulus provided to the user during the first test while the GUI displays an instruction on the interface screen requesting the user provide a second selection input indicating when the user senses the stimulus provided by the wearable device during the second test to determine a final sensory threshold value for the foot of the user;

determining the sensory threshold information of the user based on the intensity of the stimulus provided to the user at a time when the second selection input was received from the user during the second test; and controlling a plurality of vibrators included in the wearable device based on the sensory threshold information to provide the stimulus to the user.

20. The method of claim 19, wherein the sensory threshold information includes a sensory threshold value determined through the sensory threshold test for each of a left forefoot of the user, a left rearfoot of the user, a right forefoot of the user, and a right rearfoot of the user.

21. A non-transitory computer-readable medium comprising computer readable instructions that, when executed by a computer, causes the computer to perform the method of claim 1.

22. A terminal device comprising:

a communication device configured to communicate with a wearable device included in a shoe worn by a user; and a processor configured to, control a graphical user interface (GUI) of terminal device to display an interface screen requesting a user input from the user to begin a sensory threshold test, perform the sensory threshold test on the user in response to receipt of the user input to begin the sensory threshold test, the performing the sensory threshold test including, performing a first test by instructing the wearable device to provide a stimulus to the user while controlling the GUI such that an intensity of the stimulus provided to the user increases while the GUI displays an instruction on the interface screen requesting the user receiving the stimulus to provide a selection input indicating when the user senses the stimulus provided by the wearable device during the first test to determine a reference sensory threshold value for a foot of the user, and performing, a second test after the first test by instructing the wearable device to provide the stimulus to the user while controlling the GUI such that the intensity of the stimulus provided to the user during the second test increases at a different rate from the intensity of the stimulus provided to the user during the first test while the GUI displays an instruction on the interface screen requesting the user provide a second selection input indicating when the user senses the stimulus provided by the wearable device during the second test to determine a final sensory threshold value for the foot of the user, determine sensory threshold information of the user based on the intensity of the stimulus provided to the user at a time when the second selection input was received from the user during the second test, and transmit, via the communication device, the sensory threshold information to the wearable device.

23. The terminal device of claim 22, wherein the processor is configured to determine the sensory threshold information by determining, through the sensory threshold test, a sensory threshold value of each of a left forefoot of the user, a left rearfoot of the user, a right forefoot of the user, and a right rearfoot of the user.

24. A wearable device included in a shoe worn by a user, the wearable device configured to communicate with a terminal device, the terminal device including a graphical user interface (GUI), the wearable device comprising:

at least one vibrator configured to generate a vibration;

a communication device configured to receive, from the terminal device, sensory threshold information of the user, the sensory threshold information determined via a sensory threshold test, the sensory threshold test including (i) a first test in which the wearable device provides a stimulus to the user while the terminal devices controls the GUI such that an intensity of the stimulus provided to the user increases while the GUI displays an instruction on an interface screen requesting the user receiving the stimulus to provide a selection input indicating when the user senses the stimulus provided by the wearable device during the first test to determine a reference sensory threshold value for a foot of the user, (ii) a second test performed after the first test in which the wearable device provides the stimulus to the user while controlling the GUI such that the intensity of the stimulus provided to the user during the second test increases at a different rate from the intensity of the stimulus provided to the user during the first test while the GUI displays an instruction on the interface screen requesting the user provide a second selection input indicating when the user senses the stimulus provided by the wearable device during the second test to determine a final sensory threshold value for the foot of the user, and (iii) a determination of the sensory threshold information of the user based on the intensity of the stimulus provided to the user at a time when the second selection input was received from the user during the second test; and a controller configured to control the at least one vibrator to generate the vibration based on the sensory threshold information to provide the stimulus to the user.

25. The wearable device of claim 24, wherein the at least one vibrator is configured to generate the vibration such that an intensity of the vibration is less than a sensory threshold of the user wearing the wearable device determined based on the sensory threshold information.

* * * * *